United States Patent
Lee (10) Patent No.: US 8,790,500 B2
(45) Date of Patent: Jul. 29, 2014

(54) BIOSENSOR AND READOUT METER

(75) Inventor: Jin-Woo Lee, Gyeonggi-do (KR)

(73) Assignee: Ceragem Medisys Inc. (KR)

( * ) Notice: Subject to any disclaimer, the term of this patent is extended or adjusted under 35 U.S.C. 154(b) by 669 days.

(21) Appl. No.: 12/676,183

(22) PCT Filed: Aug. 7, 2008

(86) PCT No.: PCT/KR2008/004591
§ 371 (c)(1),
(2), (4) Date: Mar. 3, 2010

(87) PCT Pub. No.: WO2009/031761
PCT Pub. Date: Mar. 12, 2009

(65) Prior Publication Data
US 2010/0170791 A1    Jul. 8, 2010

(30) Foreign Application Priority Data
Sep. 4, 2007   (KR) .................. 10-2007-0089614

(51) Int. Cl.
*G01N 27/327*    (2006.01)
(52) U.S. Cl.
CPC .................................. *G01N 27/327* (2013.01)
USPC .................. 204/403.01; 422/68.1; 422/82.01; 435/287.1
(58) Field of Classification Search
CPC .................................................. G01N 27/327
USPC ............ 204/403.01–403.15; 205/775, 777.5, 205/778, 792; 600/309–349; 422/68.1, 422/82.01; 435/287.1
See application file for complete search history.

(56) References Cited

U.S. PATENT DOCUMENTS

| | | | |
|---|---|---|---|
| 4,714,874 A * | 12/1987 | Morris et al. .................. | 324/601 |
| 6,827,829 B2 * | 12/2004 | Kawanaka et al. ...... | 204/403.02 |
| 2003/0042150 A1 | 3/2003 | Ryu et al. | |
| 2005/0279647 A1 * | 12/2005 | Beaty ............................ | 205/792 |
| 2006/0099703 A1 | 5/2006 | Choi et al. | |
| 2006/0144704 A1 * | 7/2006 | Ghesquiere et al. ..... | 204/403.01 |
| 2007/0015286 A1 * | 1/2007 | Neel et al. ..................... | 436/149 |

FOREIGN PATENT DOCUMENTS

EP    1 764 153 A2    3/2007
KR    20-01409396    2/2006

* cited by examiner

*Primary Examiner* — Jennifer Dieterle
(74) *Attorney, Agent, or Firm* — Michael Morency; Foley & Lardner LLP (57) ABSTRACT

The present invention relates to a biosensor for selectively performing quantitative analysis on a specific substance contained in a biological sample and a readout meter using the same. The inventive biosensor comprises an electrode for recording identification information of the biosensor thereon. The electrode has an electrode pattern and a plurality of contact points formed thereon according to the identification information, and the identification information is recorded on the electrode based on the ratio of resistances between the plurality of contact points. According to the present invention, various items of identification information such as information on recognition of electrical connection between the contact points of the biosensor and a readout meter, the kind of a target substance, measurement conditions, production information of the biosensor, analysis information of the target substance, user information, available meter information and the like are automatically recognized by the readout meter through the electrodes.

16 Claims, 7 Drawing Sheets

BIOSENSOR AND READOUT METER

RELATED APPLICATIONS

This application is the U.S. National Stage of International Application No. PCT/ KR2008/004591, filed Aug. 7, 2008, which claims the priority benefit of Korean Application No. 10-2007-0089614, filed Sept. 4, 2007. The entire teachings of the above applications are incorporated herein by reference.

TECHNICAL FIELD

The present invention relates to a biosensor for selectively performing quantitative analysis on a specific substance contained in a biological sample and a readout meter using the same, and more particularly, to a biosensor which including electrodes for allowing the readout meter to automatically recognize various information such as information on recognition of electrical connection between contact points of a biosensor and a readout meter, the kind of a target substance, measurement conditions, production information of the biosensor, analysis information of the target substance, user information, available meter information and the like.

BACKGROUND ART

A biosensor is an analytical device which utilizes an intrinsic function of a biological body to examine properties of biological materials. The biosensor is excellent in sensitivity and reaction specificity since it uses a biological material as a detecting element. Thus, the biosensor is used in a variety of fields such as medical/medicine (clinical chemistry analysis and treatment), process measurement of bio-industry, environmental measurement, stability evaluation of chemicals and the like, and its applicable range is being continuously extended. particularly, the biosensor is widely used to analyze a biological sample including blood in the medical diagnosis field. The biosensor is classified into an enzyme analysis type and an immunity analysis type according to the kind of a detecting element, and is classified into an optical biosensor and an electrochemical biosensor according to a method of quantitatively analyzing a target substance in a biological sample.

The biosensor of enzyme analysis type employs specific reactions between enzyme and substrate, or specific reactions between enzyme and enzyme inhibitor. The biosensor of immunity analysis type employs specific reactions between antigen and antibody. Thus, the biosensor of immunity analysis type is widely used in hospital and clinical chemistry analysis fields since it is excellent in measurement sensitivity and can rapidly obtain a result. particularly, a target substance can be quantitatively analyzed directly on the spot through a disposable biosensor and a small-sized readout meter in the point-of-care testing (POCT).

The optical biosensor has been most widely used, and it can measure a concentration of a target substance through measurement of optical transmittance, optical density or wavelength change. The optical biosensor has an advantage in that the reaction mechanism of various substances to be analyzed has been already found, and a variation in the measurement time is small since measurement is performed after reaction for a sufficient time. However, the optical biosensor entails problems in that it has a relatively long measurement time and requires a large quantity of samples as compared to the electrochemical biosensor. Also, the optical biosensor encounters drawbacks in that a measurement result is affected by turbidity of the sample and miniaturization of an optical section is difficult. The electrochemical biosensor detects an electrical signal obtained from a reaction to measure a concentration of a target substance.

The electrochemical biosensor has advantages in that amplification of a signal is possible with only an infinitesimal sample, its miniaturization is easily achieved, a measurement signal can be stably acquired, and its incorporation with information communication devices is easily accomplished. However, it has still shortcomings in that an electrode process is required, the production cost is high and the measurement signal is very susceptible to the reaction time.

The use of a readout meter requires that a biosensor should be inserted into the readout meter. When the biosensor is inserted into the readout meter, the meter recognizes the insertion of the biosensor thereto and analyzes a target substance in a sample. In this case, it is required that a calibration code programmed in the readout meter should be selected, and information on target substance to be detected by the inserted biosensor should be provided. Thus, a conventional biosensor and readout meter employs a scheme of transforming a biosensor structure and electrode, or allowing a user to directly enter information to the readout meter.

EP 0471986 discloses a quantitative analysis system which measures the level of glucose in blood using a disposable biosensor. In the above European Patent, a resistance value between a pair of electrodes is measured to determine whether blood is injected into the biosensor so as to commence the measurement of the blood glucose level, and a resistor is connected between the electrodes to change a measurement mode for the meter to select a required calibration curve. However, this European Patent has an inconvenience in that electrodes connected with a resistor must be used independently of the biosensor. U.S. Pat. No. 4,999,582 to Parks et al. discloses a biosensor electrode excitation circuit which determines whether a biosensing test cell as a biosensor has been inserted into a biosensing instrument, and applies an excitation voltage between a pair of electrodes of the test cell based on the determination result. U.S. Pat. No. 5,438,271 to White et al. discloses a readout meter determines whether a sample strip as a biosensor has been properly inserted into the readout meter, and distinguishes whether a sample strip is for test or for calibration of the readout meter. U.S. Pat. No. 6,599,406 B1 to Kawanaka et al. discloses a concentration measuring apparatus which determines the kind of a target component to be measured and whether the test strip has been inserted into the measuring apparatus, by forming a separate identifying electrode. U.S. Pat. No. 6,827,829 B2 to Kawanaka et al. discloses a test strip for concentration measuring apparatus in which a separate reagent identifying electrode is formed on the test strip in various fashions to determine the kind of a target component to be measured and whether the test strip has been inserted into the measuring apparatus.

As mentioned above, the conventional biosensors and the readout meters implement functions of determining whether the biosensors have been inserted into the readout meters, the kind of the biosensors, analyte, and the like. However, there is a functional limitation since these functions are separately implemented, but not integrally implemented on the biosensors.

DISCLOSURE OF INVENTION

Technical Problem

Accordingly, the present invention has been made to overcome the above-mentioned problems occurring in the prior art, and it is an object of the present invention to provide a biosensor including electrodes formed thereon, the electrodes each having a plurality of contact points formed thereon, for allowing the readout meter to automatically recognize various information such as information on recognition of electrical connection between the contact points of the biosensor and a readout meter, the kind of a target substance, measurement conditions, production information of the biosensor, analysis information of the target substance, user information, available meter information and the like.

Technical Solution

To accomplish the above objects according to one aspect of the present invention, there is provided a biosensor for use with a readout meter to measure a concentration of a target substance and comprising an electrode for recording identification information of the biosensor thereon, wherein the electrode has an electrode pattern and a plurality of contact points formed thereon according to the identification information, and wherein the identification information is recorded on the electrode based on the ratio of resistances between the plurality of contact points.

According to another aspect of the present invention, there is provided a biosensor for use with a readout meter, the biosensor being adapted to measure a concentration of a target substance and comprising an electrode for recording identification information of the biosensor thereon, wherein the electrode has an electrode pattern and a plurality of contact points formed thereon according to the identification information, and wherein the identification information is recorded on the electrode based on a resistance value between the contact points.

According to still another aspect of the present invention, there is provided an electrochemical biosensor for use with a readout meter, the biosensor being adapted to measure a concentration of a target substance in an electrochemical method and comprising a plurality of electrodes, wherein at least one of the electrodes has an electrode pattern and a plurality of contact points formed thereon according to identification information, and wherein the identification information is recorded on the electrode based on the ratio of resistances between the plurality of contact points.

According to yet another aspect of the present invention, there is provided an electrochemical biosensor for use with a readout meter, the biosensor being adapted to measure a concentration of a target substance in an electrochemical method and comprising a plurality of electrodes, wherein at least one of the electrodes has an electrode pattern and a plurality of contact points formed thereon according to identification information, and wherein the identification information is recorded on the electrode based on a resistance value between the contact points.

According to a further aspect of the present invention, there is provided a readout meter for use with a biosensor, the biosensor being adapted to measure a concentration of a target substance, comprising: identification information detection part electrically connected to a plurality of contact points formed on the biosensor for measuring the ratio of resistances between the contact points and detecting identification information of the biosensor; concentration measurement part for measuring the concentration of a target substance applied to the biosensor; analysis part for analyzing a measurement result of the concentration measurement part based on the detected identification information; and display part for displaying an analysis result of the analysis part.

According to a still further aspect of the present invention, there is provided a biosensor system comprising a biosensor and a readout meter, wherein the biosensor comprises an electrode for recording identification information of the biosensor thereon, the electrode having an electrode pattern and a plurality of contact points formed thereon according to identification information, and the identification information being recorded on the electrode based on the ratio of resistances between the plurality of contact points, wherein the readout meter comprises: identification information detection part electrically connected to a plurality of contact points formed on the biosensor for measuring the ratio of resistances between the contact points and detecting identification information of the biosensor; concentration measurement part for measuring the concentration of a target substance applied to the biosensor; analysis part for analyzing a measurement result of the concentration measurement part based on the detected identification information; and display part for displaying an analysis result of the analysis part.

Advantageous Effects

According to the present invention, various information such as information on electrical connection between the contact points of a biosensor and a readout meter, the kind of a target substance, measurement conditions, production information of the biosensor, analysis information of the target substance, user information, available meter information and the like can be recorded on the electrodes using the ratio of resistances between contact points formed on the electrodes of the biosensor. Further, the identification information can be automatically provided to the readout meter upon the insertion of the biosensor into the readout meter. Therefore, it is possible to eliminate an inconvenience for a user to have to separately input identification information to the readout meter.

BEST MODE FOR CARRYING OUT THE INVENTION

The above objects, features, benefits and advantages will be apparent from the following detailed description taken in conjunction with the accompanying drawings. Accordingly, it is to be noted that a person skilled in the art to which the present invention pertains will easily carry out the technical spirit of the present invention. Also, in the description, details on well-known techniques and constitution associated with the present invention may be omitted to avoid unnecessarily obscuring the invention.

A preferred embodiment of the present invention will now be described in detail with reference to the attached drawings.

Figure 1:
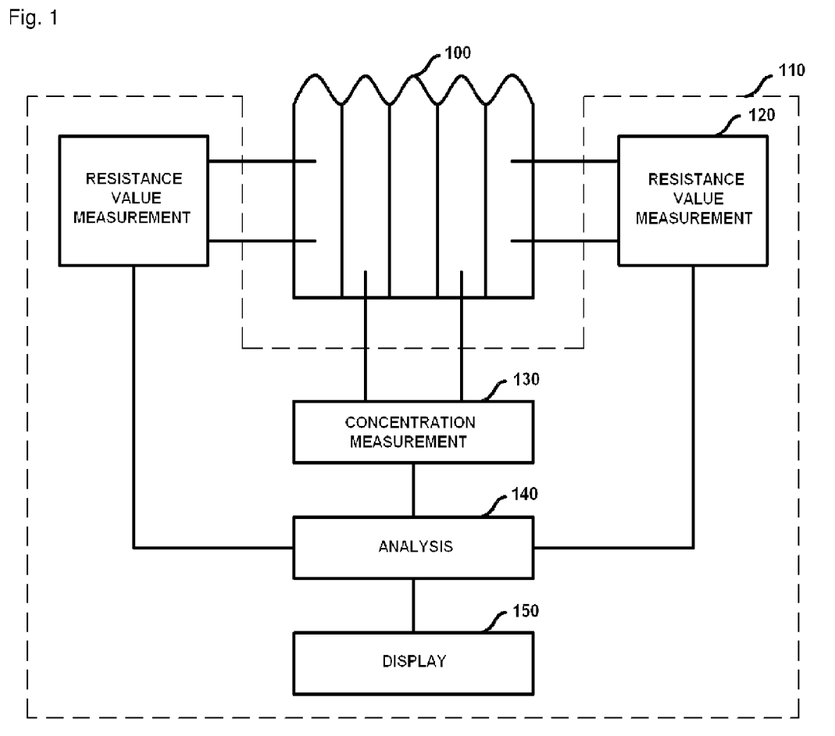
FIG. 1 illustrates the constitution of an exemplary readout meter to which the present invention is applied.

FIG. 1 is a block diagram showing the constitution of a readout meter to which the present invention is applied.

As shown in FIG. 1, the readout meter 110 includes a resistance value measurement section 120, a concentration measurement section 130, an analysis section 140 and a display section 150.

The identification information detection part serves to measure identification information of each biosensor 100 through a resistance value measurement section 120. The identification information detection part is electrically connected to a plurality of contact points formed on the biosensor and measures resistance values of the contact points to calculate the ratio of the resistance values between the contact points. Since the identification information assigned to each biosensor is determined depending on the resistance ratio, it is detected through the ratio of resistances between the contact points.

The concentration measurement part serves to measure the concentration of an analyte applied to the biosensor through the concentration measurement section 130. In case where the biosensor is an electrochemical biosensor, the concentration measurement part converts a biochemical signal into an electrical signal to detect electrical current by a reaction due to application of current across electrodes formed on the biosensor. In case where the biosensor is an optical biosensor, the concentration measurement part converts a biochemical signal into an optical signal to detect the strength of light irradiated to and reflected from the biosensor.

The analysis part 140 serves to present the measurement conditions of the concentration measurement section 130 and analyze the measurement result based on the identification information. If the kind of a target substance to be analyzed is determined based on the identification information detected by the resistance value measurement section 120, the analysis part 140 presents the measurement conditions depending on the kind of target substance. If the strength of light or current is measured depending on the measurement conditions, the concentration of the target substance is calculated based on the measured strength of light or current. At this time, the analysis part 140 may indicates or selects a curve for property calibration.

The display part, i.e., the display section 150 displays an analysis result of the analysis part 140.

The present invention allows the identification information to be recorded on the electrode based on the ratio of resistances between the plurality of contact points formed on the electrode. An electrode having a relatively large width may be formed of a thick film or a thin film. The thick film has a thickness of more than several hundreds of micrometers (μm), and the thin film has a thickness of 1 μm or less than 1 μm. The electrode may be formed by screen printing, plating, sputtering and the like. The screen printing is performed in such a fashion that an electrode pattern is formed by a silk screen. The plating is performed in such a fashion that a desired electrode pattern is first drawn on a conductive material using a screen printing or lithography method, and then a desired electrode material is selected and is plated by means of an electrolysis or non-electrolysis method to thereby form the pattern. Currently, the sputtering method is widely used, and there are proposed a method in which the pattern is formed while being subjected to the sputtering using a shadow mask, and a method in which the pattern is formed using lithography or laser after being subjected to the sputtering. The thick film is mainly formed by the screen printing and the plating, and the thin film is mainly formed by the sputtering.

A designer may form a desired electrode pattern using various methods as mentioned above, and resistance values of each electrode pattern vary depending on the thickness of the electrode and the shape of the pattern. In this case, there is caused a problem in that there occurs a deviation in the thickness of the electrode and the size of the electrode pattern depending on a process method and a process area. In this regard, a problem is caused in that there is a slight difference in the thickness of the electrode every process. Also in case of a large-area process, although electrodes are formed by the same process, there is a sight difference in the thickness of the electrodes depending on the position of the electrodes, making it difficult to obtain a uniform absolute value of an electrode resistance. particularly, in case of the thin film having a relatively small thickness as compared to the thick film, the thin film does not have a uniform resistance value due to a great deviation in thickness thereof. Thus, it is important to form an electrode having a uniform thickness on a large area. To this end, the present invention allows the identification information to be recorded on the electrode by using the ratio of resistances between the contact points.

Figure 2:
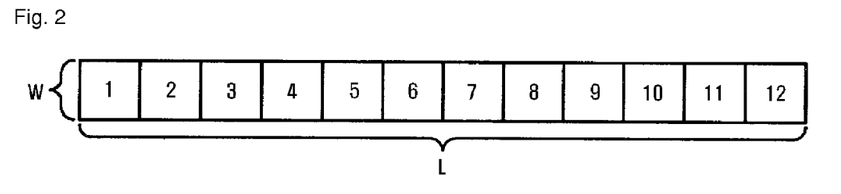
FIG. 2 illustrates an electrode used for explaining a resistance measurement method according to an embodiment of the present invention.

FIG. 2 is a schematic view showing an electrode used for explaining a resistance measurement method according to an embodiment of the present invention, wherein the electrode is viewed from the top. Assuming that the electrode is formed to a uniform thickness, a resistance of the electrode is determined in proportional to the area of the electrode as shown in the following Equation 1.

$$R = \rho \frac{L}{A} = \rho \frac{L}{Wt} = \frac{\rho}{t} \frac{L}{W} = R_s \frac{L}{W} \qquad \text{[Equation 1]}$$

where R denotes a resistance, p denotes a resistivity, A denotes a cross section, t denotes a thickness of electrode (conductor), W denotes a width of electrode, L denotes a length of electrode, and Rs denotes a sheet resistance. That is, the resistivity and the thickness are constant, the size of the resistance is in proportional to the number of L/W (the number of regular triangles in which one side has a length of W). Thus, if the electrode consists of 12 regular triangles, L/W is 12 and a resistance of the electrode is 12 times as many as Rs.

In the course of manufacturing the biosensor of a large area, a problem occurs in that the thickness of the electrode is non-uniform. However, ever in case where the biosensor of a large area is fabricated, a resistance at two places adjacent to each other within a near distance of several centimeters (cm) is relatively uniform. Thus, when taking into consideration that the size of a typically fabricated biosensor is about 1 cm×3-5 cm, it can be seen that the thickness of an electrode in one biosensor is uniform. Thus, although there is a difference in thickness of the electrode of each biosensor, if the ratio between resistance values is used instead of resistance values, the resistance ratios for the same electrode patterns in each biosensor will be equal. By doing so, it is possible to overcome a problem caused by a difference in resistance values due to non-uniformity of the electrode thickness which is apt to occur in the large-area process.

Figure 3:
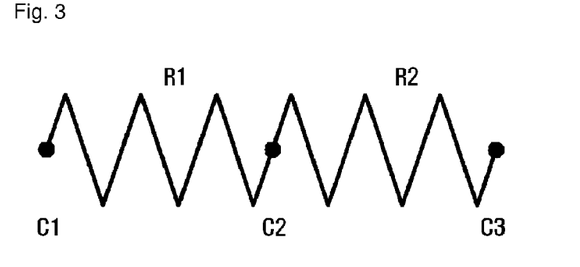
FIG. 3 illustrates resistances and contact points used for explaining a resistance ratio measurement method according to another embodiment of the present invention.

FIG. 3 is a schematic view showing resistances and contact points used for explaining a resistance ratio measurement method according to an embodiment of the present invention.

As shown in FIG. 3, if a resistance between two contact points C1 and C2 is R1, and a resistance between two contact points C2 and C3 is R2, the ratio between the resistances R1 and R2 can be calculated by the following Equation 2:

$$\text{Ratio} = \frac{R2}{R1} \qquad \text{[Equation 2]}$$

Also, the following Equation 3 can be obtained using Equation 1 and Equation 2:

$$\text{Ratio} = \frac{R2}{R1} = \frac{\rho_2 \frac{L_2}{W_2}}{\rho_1 \frac{L_1}{W_1}} = \frac{W_1}{W_2} \qquad \text{[Equation 3]}$$

That is, assuming that the distances between the respective contact points C is equal, the resistance ratio can be easily determined by the width of the conductor between the respective contact points. Thus, assuming that the thickness of the thin film of the electrode is uniform, it can be seen that when the geometrical structure of the electrode pattern is used, a resistance value is in proportional to an area of the electrode. Accordingly, in the present invention, the identification information is assigned to the electrode by using this proportional relationship between the resistance value and the electrode area or the resistance values between the contact points. The contact points may be contact points which are arbitrarily formed on the electrode in order for a user to obtain the ratio of resistances, and may be contact points to which a reaction voltage of the electrochemical biosensor is applied. That is, the ratio of resistances between the contact points can be obtained by using all the contact points existing on the biosensor.

A method of forming the contact points on the biosensor is roughly divided into three types. A first method is to form a separate electrode on an optical biosensor and the like, and create contact points on the formed separate electrode to thereby record the identification information on the electrode. A second method is to form a separate electrode on an electrochemical biosensor, and create contact points on the formed separate electrode to thereby record the identification information on the electrode. In this case, the separate electrode may be formed integrally with various electrodes such as a reference electrode and the like present on the electrochemical biosensor. A third method is to form the contact points on various electrodes such as a reference electrode, a working electrode or the like present on the electrochemical biosensor. In this case, since an existing electrode is used, a separate electrode needs not to be formed.

Figure 4:
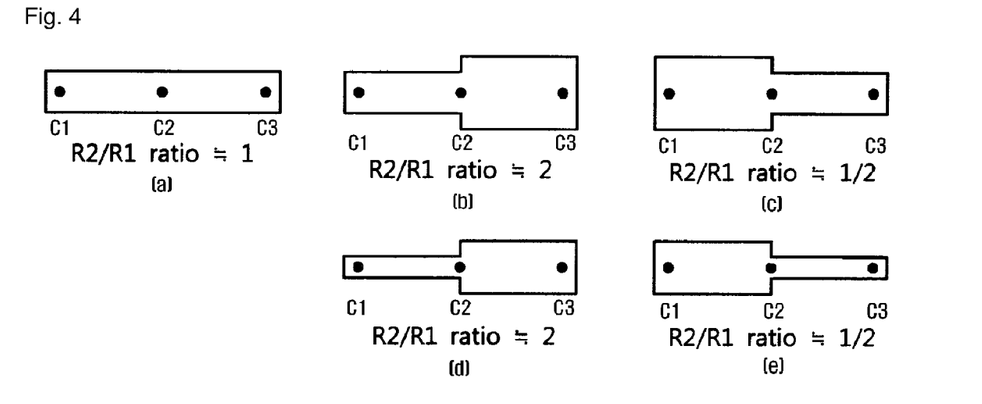
FIG. 4 is a plan view showing electrodes each having three contact points according to one embodiment of the present invention.

FIG. 4 is a plan view showing electrodes each having three contact points according to one embodiment of the present invention.

If the contact points C1, C2, and C3 are present on each electrode, a resistance between contact points C1 and C2 is R1 and a resistance between contact points C2 and C3 is R2, the ratio of the resistances R1 and R2 can be obtained. In case of an electrode shown in FIG. 4(a), the distance between the contact points C1, C2 and C3 is constant and the area of the electrode between the contact points C1, C2 and C3 is also constant. Thus, the ratio of the resistances R1 and R2 is 1. In case of an electrode shown in FIG. 4(b), since the area of the electrode between the contact points C1 and C2 is half that of the electrode between the contact points C2 and C3, the ratio of the resistances R1 and R2 is 2. Besides these, as in the electrodes shown in FIGS. 4(c), (d) and (e), the ratio of resistances between the respective contact points can be obtained by the proportional relationship of the area between the respective contact points, and various electrode patterns having the same resistance ratio can be formed.

Figure 5:
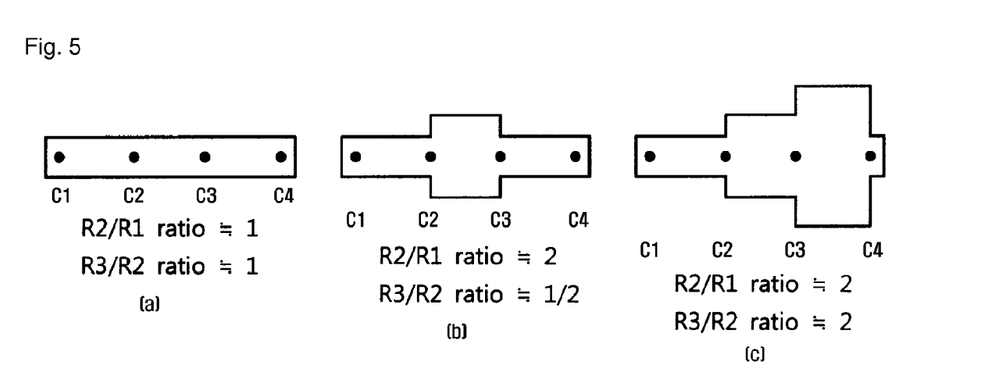
FIG. 5 is a plan view showing electrodes each having four contact points according to one embodiment of the present invention.

FIG. 5(a) to (c) are plan views showing electrodes each having four contact points according to one embodiment of the present invention.

As shown in FIG. 5(a) to (c), since the contact points C1, C2, C3, C4 are present on each electrode, a plurality of resistance ratios can be used, but not one resistance ratio. If the resistance ratio between the contact points C1 and C2 is R1, the resistance ratio between the contact points C2 and C3 is R2, and the resistance ratio between the contact points C3 and C4 is R3, two resistance ratios between the respective contact points can be obtained. Using such a principle, much more resistance ratios can be obtained. By doing so, much more identification information can be recorded on the electrode.

Table 1 shows a method of assigning the identification information according to one embodiment of the present invention. The identification information is recorded on the electrode in such a fashion that the electrode is assigned with one identification information for a combination of the ratio of resistances between the plurality of contact points and a resistance value between the contact points.

TABLE 1

| Function No. | R1(ohm) | R2/R1 |
|---|---|---|
| 1 | 10 | 1 |
| 2 | 10 | 2 |
| 3 | 10 | 0.5 |
| ... | ... | ... |
| N | 20 | 1 |
| N + 1 | 20 | 3 |
| N + 2 | 20 | 2 |

According to the present invention, the resistance ratio as well as the resistance value itself may be used to record the identification information on the electrode, and the resistance ratio and as the resistance value can be simultaneously used to record the identification information on the electrode. A function number is assigned for a combination of the resistance ratio and the resistance value. Different identification information is assigned to the electrode according to each function number. Thus, the assignment of a limitless function number is possible, and this allows various identification information to be recorded on the electrode. In addition, the function number may be assigned for a predetermined range of the ratio of resistances between the plurality of contact points or the resistance values between the plurality of contact points.

For instance, a function number 1 may be assigned for the resistance value 5 to 15, and a function number 2 may be assigned for the resistance value 16 to 25. Thus, the identification information can be recorded on the electrode without being affected by a small error which may occur during the process.

Figure 6:
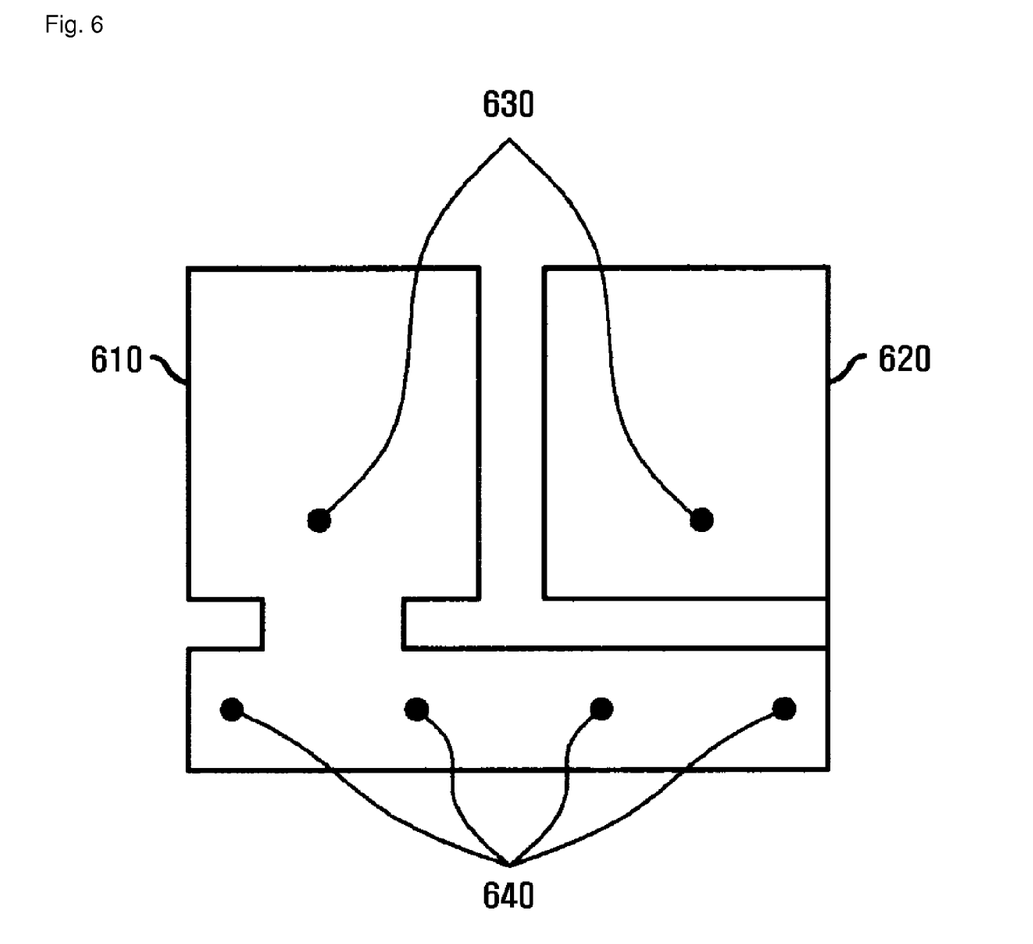
FIG. 6 is a plan view showing an indicator electrode formed according to one embodiment of the present invention.

FIG. 6 is a plan view showing an indicator electrode formed according to one embodiment of the present invention.

In case of an electrochemical biosensor, a plurality of electrodes including a reference electrode and a working electrode are formed on the biosensor. Thus, various electrodes formed on the electrochemical biosensor, for example, the identification information can be recorded on the reference electrode or the working electrode having contact points formed thereon. Since the biosensor of the present invention allows the identification information to be recorded on the electrode using the ratio of resistances between the contact points, it may be not necessarily formed independently of an existing electrode. Since the biosensor of the present invention is separated from a reaction element, it does not affect a reaction itself. Thus, a process can be simplified and a process cost can also be saved by using an existing electrode and connecting the existing electrode to a separate electrode to form the biosensor. Thus, as shown in FIG. 6, a separate electrode pattern 610 can be formed by connected with a reference electrode and a working electrode 620 can be formed separately. A contact point 630 is formed on the reference electrode and the working electrode, respectively, and four contact points 640 are formed on the separate electrodes.

Figure 7:
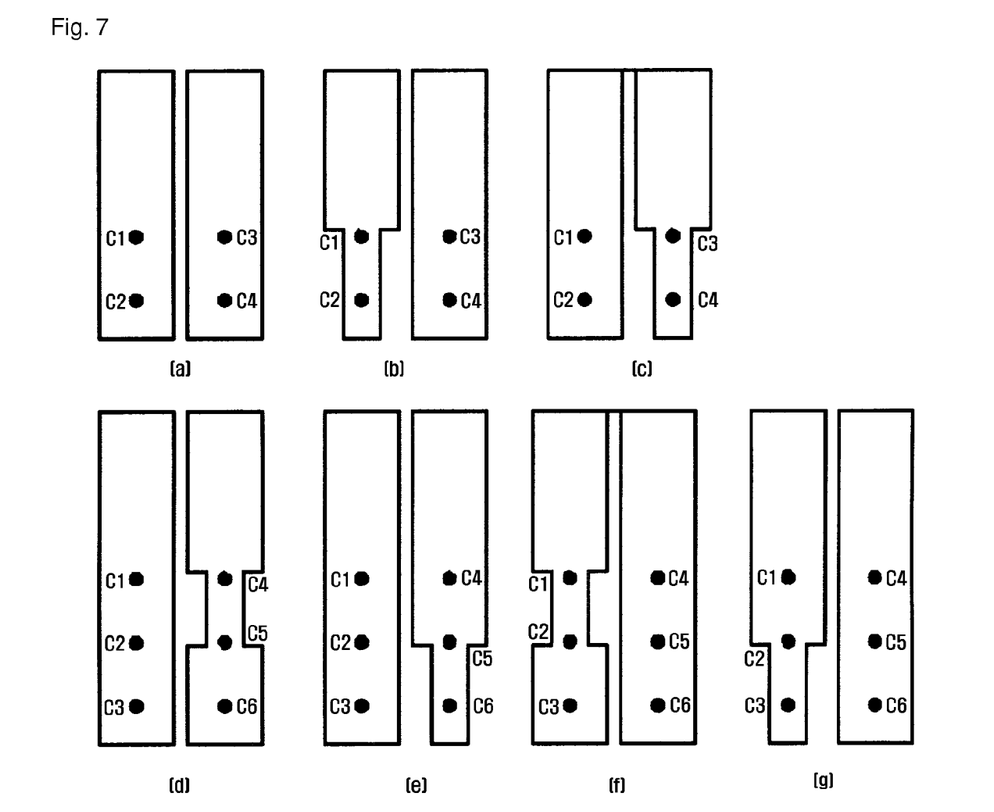
FIG. 7 is a plan view showing various electrodes of electrochemical biosensor each having contact points according to one embodiment of the present invention.

FIGS. 7(*a*) to (*g*) are plan views showing different electrodes each having contact points formed in an electrochemical biosensor according to one embodiment of the present invention.

As shown in FIGS. 7(*a*) to (*g*), the contact points do not need to be necessarily formed on a separate electrode, and the biosensor can be implemented using a plurality of electrodes formed on the electrochemical biosensor. For instance, the contact points are formed in a working electrode or a reference electrode, and a variety of identification information can be recorded on the electrodes depending on the pattern of the electrode and the number of the contact points. FIGS. 7 (*a*), (*b*) and (*c*) show embodiments in which two contact points are formed on each electrode and the identification information is recorded on the electrodes according to the pattern of the electrode. FIGS. 7(*d*),(*e*),(*f*) and (*g*) show embodiments in which three contact points are formed on each electrode and the identification information is recorded on the electrodes according to the pattern of the electrode.

Figure 8:
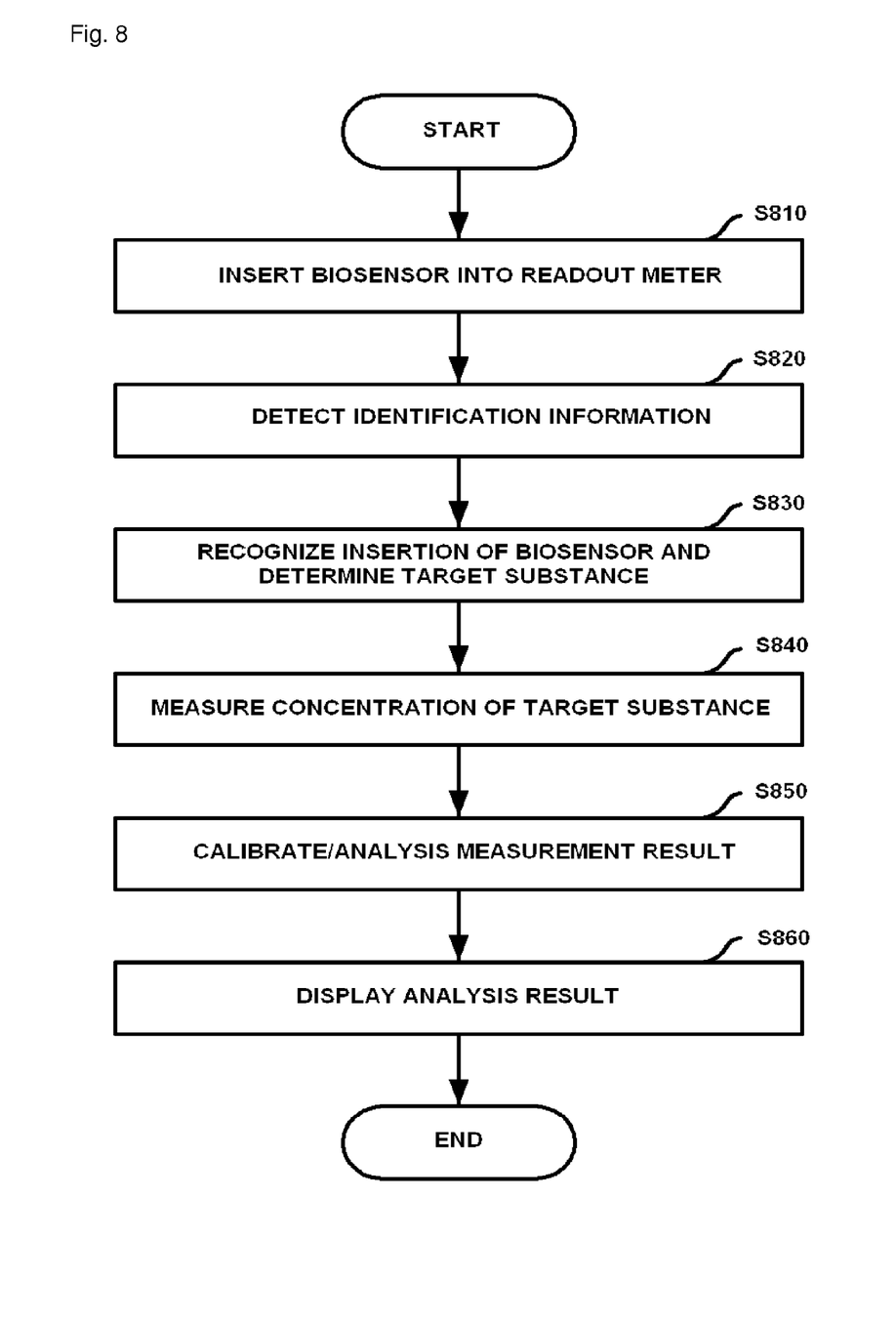
FIG. 8 is a flowchart showing the operation of a readout meter according to one embodiment of the present invention.

FIG. 8 is a flowchart showing the operation of a readout meter according to one embodiment of the present invention.

When a biosensor is inserted into a readout meter (S810), the meter is electrically connected to the contact points of the biosensor so that the ratio of resistances between the contact points formed on each electrode of the biosensor is measured. Since the identification information is assigned for the resistance ratio, the readout meter can measure the resistance ratio between the plurality of contact points so as to detect the identification information (S820). The identification information includes information on recognition of electrical connection between the contact points of the biosensor and the readout meter, the kind of a target substance, measurement conditions, production information of the biosensor, analysis information of the target substance, user information, and available meter information.

The information on recognition of electrical connection between the contact points of the biosensor and the readout meter allows the biosensor meter to recognize the insertion of the biosensor into the meter. Since there may occur the case where a user mistakenly inserts a plastic article, but not the biosensor, into the readout meter upon the use of the meter, the identification information allows the biosensor meter to be informed of that the biosensor has been inserted into the meter. Also, information on the kind of a target substance to be analyzed, for example, blood glucose, cholesterol or the like is provided, and the measurement conditions according to the kind of the target substance are informed. This is to increase accuracy of the measurement result according to the target substance. In this case, a temperature calibration, a hematocrit calibration or the like is performed. The identification information also includes production information of the biosensor. Since a substrate is produced to have a large area and then is cut into a given size in the course of production of the biosensor, there is a slight difference between properties in each lot. Thus, the production information for calibration according to each lot is provided in the form of day, time and the like. The analysis information of the target substance means a calculation equation, a calibration graph and the like used in the course of calculating the concentration of the target substance through an electrical or optical signal. The user information informs a user of which customer manufactures the biosensor inserted into the readout meter. For instance, even in case of a biosensor for measuring the concentration of the same target substance, there may be the case where the biosensors for a customer A, a customer B and a customer C are discerned, respectively. Thus, the provision of the user information allows the user to check the name of a corresponding customer of the biosensor. Further, the available meter information informs a user of whether a corresponding biosensor is available in the biosensor meter upon the insertion of the biosensor into the readout meter. For instance, the biosensor for measuring the concentration of the same target substance cannot use a component "a" for the reason of the patent and the like in the U.S., but the component "a" may be available in South-East Asia. In this case, since the biosensor including the component "a" should not be allowed to be used in readout meters being sold in the U.S., the available meter information can provide the user with information that the biosensor cannot be used in a biosensing meter of a specific model (S830).

The readout meter measures the concentration of the target substance applied to the biosensor based on the identification information (S840). The electrochemical biosensor converts a biochemical signal into an electrical signal to perform a detection function, a voltage is applied across the electrode formed on the biosensor to detect electric current by a reaction and measure the concentration of the target substance.

The optical biosensor converts a biochemical signal into an optical signal to perform a detection function, and measures the concentration of the target substance based on the strength of light irradiated to and reflected from the biosensor. When the concentration of the target substance is measured, a measurement result is calibrated and analyzed according to the identification information (S850). After the analysis of the measurement result has been completed, an analysis result is displayed (S860).

Figure 9:
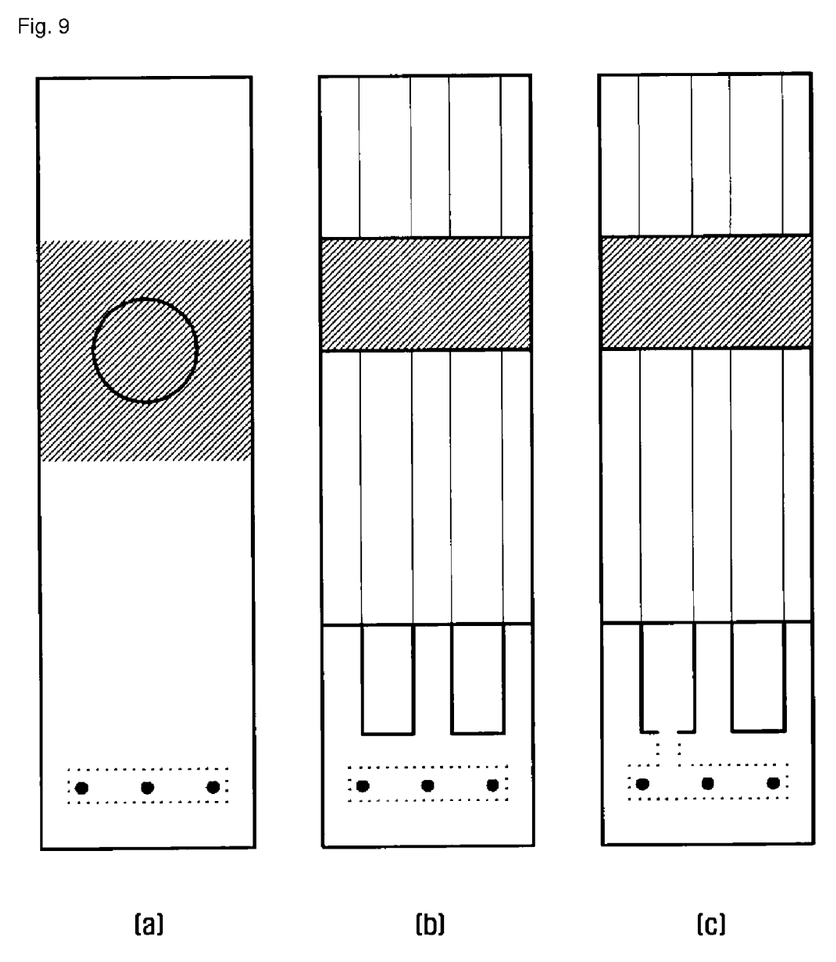
FIG. 9 is a plan view showing a biosensor according to one embodiment of the present invention.

FIG. 9(*a*) to (*c*) are plan views showing a biosensor according to one embodiment of the present invention.

FIG. 9(*a*) shows an embodiment in which an electrode is formed on an optical biosensor, FIG. 9(*b*) shows an embodiment in which a separate electrode is formed on an electrochemical biosensor, and FIG. 9(*c*) shows an embodiment in which a separate electrode is formed integrally with the electrode of the electrochemical biosensor.

The biosensor of FIG. 9(a) is an optical biosensor which includes an optical measurement element and an electrode having identification information recorded thereon independently of the optical measurement element. For instance, an electrode may be formed on a pregnancy diagnosis kit using an immuno-biosensor to deliver the identification information. The biosensor of FIG. 9(b) is an electrochemical biosensor which includes a separate electrode having identification information recorded thereon. The separate electrode is formed at a predetermined position of the electrochemical biosensor so that the contact points formed on the separate electrode is electrically connected to the readout meter to cause the identification information to be assigned by the ratio of resistances between the contact points. The biosensor of FIG. 9(c) is a modification of the electrochemical biosensor which includes a separate electrode formed thereon by the connection with electrodes, for example, a reference electrode, a working electrode and the like. The separate electrode is formed integrally with the existing electrode to that a process can be simplified and a process cost can be saved.

Figure 10:
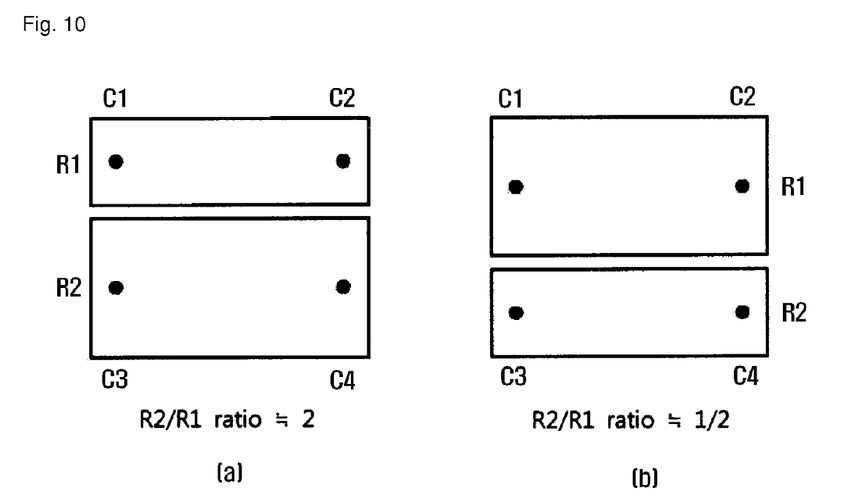
FIG. 10 is a plan view showing contact points formed on the electrodes according to one embodiment of the present invention.

FIG. 10(a) and FIG. 10(b) are plan views showing contact points formed on the electrodes according to one embodiment of the present invention.

The ratio of resistances between the contact points can be obtained by using resistance values between the contact points formed on the same electrode pattern of the biosensor as well as resistance values between the contact points formed on a separate electrode pattern. R1 denotes a resistance value between the contact points C1 and C2, R2 denotes a resistance value between the contact points C3 and C4. R1 and R2 are resistance values obtained by different electrode patterns, but the identification information can be recorded on the electrode using the ratio of the two resistance values. For instance, in case where the contact points are formed using the reference electrode and the working electrode of the electrochemical biosensor, a resistance value R1 between the contact points formed on a reference electrode and a resistance value R2 between the contact points formed on a working electrode are measured respectively, and the identification information can be recorded on the electrode using the ratio of R1 and R2.

Figure 11:
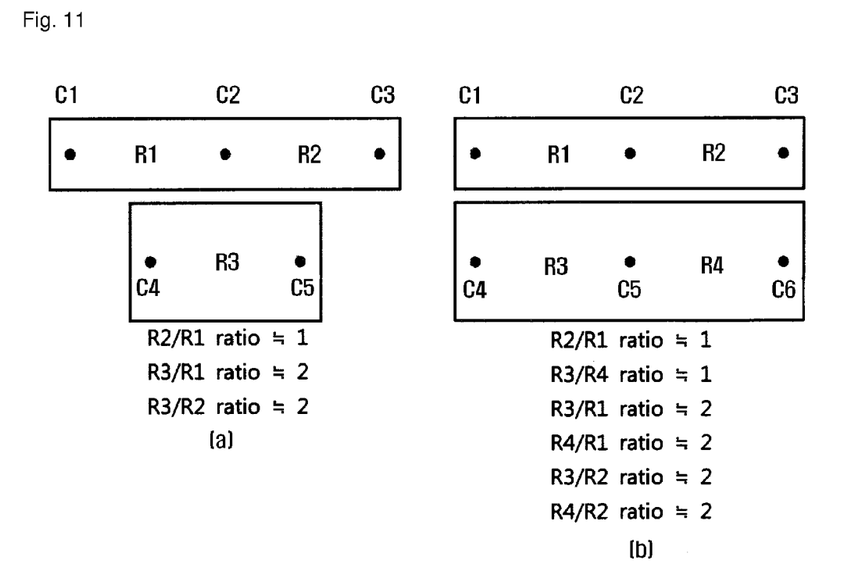
FIG. 11 is a plan view showing modified contact points formed on the electrodes according to one embodiment of the present invention.

FIG. 11(a) and FIG. 11(b) are plan views showing modified contact points formed on the electrodes according to one embodiment of the present invention.

In FIG. 11(a), R1 denotes a resistance value between the contact points C1 and C2, and R2 denotes a resistance value between the contact points C2 and C3. Also, R3 denotes a resistance value between the contact points C4 and C5. In FIG. 11(b), R1 denotes a resistance value between the contact points C1 and C2, and R2 denotes a resistance value between the contact points C2 and C3. R3 denotes a resistance value between the contact points C4 and C5, and R4 denotes a resistance value between the contact points C5 and C6. In FIG. 11(a), the identification information can be recorded on the electrode using the ratio (R2/R1) of resistance values between the contact points formed on the same electrode pattern. Besides, the identification information can be recorded on the electrode using the ratios (R3/R1, R3/R2) of resistance values between the contact points formed on the different electrode patterns. For instance, in case where the contact points are formed using the reference electrode and the working electrode of the electrochemical biosensor, a resistance values R1 and R2 between the contact points formed on the reference electrode and a resistance value R3 between the contact points formed on the working electrode are measured respectively, and then the identification information can be recorded on the electrode using the ratios (R2/R1, R3/R1 and R3/R2) of resistance values. Thus, as in FIG. 11(b), in case where a plurality of contact points is formed on the electrode, much more identification information can be recorded on the electrode.

While the preferred embodiment in accordance with the present invention has been described above, it is merely an exemplary embodiment and the present invention is not limited thereto. It will be apparent to those skilled in the art that the embodiment of the present invention can be changed or modified to have other specific forms without departing from the scope and spirit of the invention, other than the above-described embodiment. Therefore, the scope of the invention should be defined by only the appended claims and their equivalents, but not the above-mentioned embodiment.

The invention claimed is:

1. A biosensor for use with a readout meter to measure a concentration of a target substance, the biosensor comprising:
   at least one electrode for recording identification information of the biosensor thereon,
   wherein a plurality of contact points formed along a length of the electrode according to the identification information,
   wherein the identification information is recorded on the electrode based on the ratio of resistances between the plurality of contact points, and
   wherein the ratio of resistances is equal to a ratio of widths of the electrode between the plurality of contact points.

2. The biosensor according to claim 1, wherein the identification information of the biosensor is at least one of information on recognition of electrical connection between the contact points of the biosensor and the readout meter, the kind of the target substance, measurement conditions, production information of the biosensor, analysis information of the target substance, user information, and available meter information.

3. The biosensor according to claim 1, wherein the identification information is assigned with a predetermined range of the ratio of resistances between the plurality of contact points.

4. The biosensor according to claim 1, wherein the identification information is assigned with a combination of the ratio of resistances between the plurality of contact points and a resistance value between the contact points.

5. The biosensor according to claim 1, wherein the ratio of resistances between the plurality of contact points is obtained by using resistance values between the contact points formed on the same electrode of the biosensor.

6. The biosensor according to claim 1, wherein the ratio of resistances between the plurality of contact points is obtained by using resistance values between the contact points formed on separate electrodes of the biosensor.

7. The biosensor according to claim 1, wherein the biosensor is an electrochemical biosensor.

8. The biosensor according to claim 1, wherein the biosensor is an optical biosensor.

9. The biosensor according to claim 1, wherein the electrode has width variation.

10. An electrochemical biosensor for use with a readout meter to measure a concentration of a target substance in an electrochemical method, the electrochemical biosensor comprising:
   a plurality of electrodes, wherein a plurality of contact points formed along a length of the electrode according to identification information, and wherein the identification information is recorded on the electrode based on the ratio of resistances between the plurality of contact points, and wherein the resistance ratio is equal to a ratio of widths of the electrode between the plurality of contact points.

11. The electrochemical biosensor according to claim 10, wherein the identification information of the biosensor is at least one of information on recognition of electrical connection between the contact points of the electrochemical biosensor and the readout meter, the kind of a target substance, measurement conditions, production information of the electrochemical biosensor, analysis information of the target substance, user information, and available meter information.

12. The electrochemical biosensor according to claim 10, wherein the identification information of the biosensor is assigned with a predetermined range of the ratio of resistances between the plurality of contact points.

13. The electrochemical biosensor according to claim 10, wherein the identification information of the biosensor is assigned with a combination of the ratio of resistances between the plurality of contact points and a resistance value between the contact points.

14. The electrochemical biosensor according to claim 10, wherein the ratio of resistances between the plurality of contact points is obtained by using resistance values between the contact points formed on the same electrode of the electrochemical biosensor.

15. The electrochemical biosensor according to claim 10, wherein the ratio of resistances between the plurality of contact points is obtained by using resistance values between the contact points formed on separate electrodes of the biosensor.

16. A biosensor system comprising a biosensor and a readout meter, wherein the biosensor comprises at least one electrode for recording identification information of the biosensor thereon, a plurality of contact points formed along a length of the electrode according to the identification information, the identification information being recorded on the electrode based on the ratio of resistances between the plurality of contact points, and the resistance ratio being equal to a ratio of widths of the electrode between the plurality of contact points, wherein the readout meter comprises:

identification information detection part electrically connected to a plurality of contact points formed on the biosensor for measuring the ratio of resistances between the contact points and detecting identification information of the biosensor;

concentration measurement part for measuring the concentration of a target substance applied to the biosensor;

analysis part for analyzing a measurement result of the concentration measurement part based on the detected identification information; and display part for displaying an analysis result of the analysis part.

\* \* \* \* \*